US010477889B2

(12) United States Patent
Goldstein

(10) Patent No.: US 10,477,889 B2
(45) Date of Patent: Nov. 19, 2019

(54) SYSTEM, APPARATUS AND METHODS FOR A PARTICULATE FILTRATION

(71) Applicant: David Goldstein, Portland, OR (US)

(72) Inventor: David Goldstein, Portland, OR (US)

(*) Notice: Subject to any disclaimer, the term of this patent is extended or adjusted under 35 U.S.C. 154(b) by 0 days.

(21) Appl. No.: 15/664,575

(22) Filed: Jul. 31, 2017

(65) Prior Publication Data
US 2017/0325498 A1   Nov. 16, 2017

Related U.S. Application Data

(63) Continuation-in-part of application No. 14/594,302, filed on Jan. 12, 2015, now Pat. No. 9,895,641.

(51) Int. Cl.
| A24F 1/30 | (2006.01) |
| A24D 3/16 | (2006.01) |
| A24F 1/32 | (2006.01) |
| A24F 1/02 | (2006.01) |

(52) U.S. Cl.
CPC ............ *A24D 3/16* (2013.01); *A24F 1/02* (2013.01); *A24F 1/32* (2013.01)

(58) Field of Classification Search
CPC ...................................... A24F 1/30; A24F 3/00
See application file for complete search history.

(56) References Cited

U.S. PATENT DOCUMENTS

| 3,881,499 A | 5/1975 | Mcfadden et al. |
| 3,882,875 A | 5/1975 | Frost |
| 4,198,993 A * | 4/1980 | Martin .............. A24F 1/30 131/173 |
| 4,363,639 A | 12/1982 | Gladon |
| 8,973,585 B2 | 3/2015 | Goldstein |
| 9,352,260 B2 | 5/2016 | Goldstein |
| 9,895,641 B2 | 2/2018 | Goldstein |
| 2012/0152263 A1* | 6/2012 | Schoenfeld ........... A24F 3/00 131/186 |
| 2013/0104738 A1* | 5/2013 | Goldstein ........... B01D 53/14 95/214 |
| 2014/0130812 A1* | 5/2014 | Kling ............. A24F 47/008 131/173 |
| 2015/0374032 A1* | 12/2015 | De Gaglia ............ A24F 1/30 131/225 |

FOREIGN PATENT DOCUMENTS

DE   19621340 A1 *   2/1998   ........... A24F 1/30

OTHER PUBLICATIONS

DE 19621340 Translation; Wassong Heinrich (Year: 1998).*

* cited by examiner

*Primary Examiner* — Eric Yaary
(74) *Attorney, Agent, or Firm* — J. Curtis Edmondson

(57) ABSTRACT

The present invention relates to an improved water pipe comprising a chamber containing water in its lower portion, its upper compact cylindrical portion serving as a smoke collection reservoir; a bowl for combusting tobacco or medicinal herbs, the smoke directed through a tube to the water chamber below the water; and a mouth piece for applying suction to the interior of the chamber to inhale the smoke.

11 Claims, 5 Drawing Sheets

SYSTEM, APPARATUS AND METHODS FOR A PARTICULATE FILTRATION

CROSS REFERENCES TO RELATED APPLICATIONS

This application is a continuation-in-part (CIP) application claims under 35 U.S.C. § 120, to co-pending U.S. patent application Ser. No. 14/594,302 filed on Jan. 12, 2015. The present application is based on and claims priority from this application, the disclosure of which is hereby expressly incorporated herein by reference.

FIELD

In general, the invention relates to an improved apparatus for filtration of particulates from the smoke or vapor created in a water pipe.

BACKGROUND

U.S. Pat. No. 3,882,875 provides a vented pot-like vessel to contain water and provide a smoke chamber above the water, the smoke chamber being provided with finger controllable vents for the use of the user in diluting the smoke.

U.S. Pat. No. 3,881,499 illustrates a device with sedimentation chambers housed in the lower part of a tube.

U.S. Pat. No. 4,363,639 documents the use of single fritted disc filter.

SUMMARY

This invention prevents or substantially alleviates the aforesaid disadvantages of the prior art devices by providing a water pipe designed with compact space for the efficient filtering of the vapors before being inhaled by a user.

Accordingly, it is a primary object of the present invention to provide a novel and improved device for tobacco or medicinal herbs. Another object of the invention is to provide a controlled reservoir of gaseous effluent from combustion or vapor that is to be inhaled. A further object of the invention is to provide a water pipe whereby a volume of selectively controlled smoke may be inhaled without dilution or variation thereof during the inhalation. Another important object of the invention is to provide a water pipe which is designed to filter/scrub the gaseous vapors with a fritted glass filter before the user inhales the vapors.

A further object of the invention is to provide for the subsequent cooling of the smoke prior to inhalation.

Another further object of the invention is to provide a generally cylindrical water pipe of a size and extension readily accommodated by a user.

A further object of the invention is to provide an inbuilt water containing chamber for sedimentation and cooling of the smoke before the smoke enters a smoke inhalation pathway.

A further object of the present invention is to provide a transparent smoke chamber and transparent smoke and air transportation tubes and passages, typically made of clear transparent glass.

A further object of the invention is to provide a water pipe or bong which may be economically constructed of readily available components and materials.

These and further objects and advantages of the present invention will be apparent from the following detailed description of illustrated embodiments of the invention made with reference to the accompanying drawings.

LIST OF SELECTED REFERENCE CHARACTERS

| | |
|---|---|
| 100//300/400/500 | Water pipe |
| 200 | Closeup view |
| 110/510 | Primary tubular wall |
| 111/511 | Compact Smoke Chamber |
| 120/520 | Base |
| 130/530 | Secondary Cylindrical tubular wall |
| 135/535 | Flat surface |
| 155/555 | Gas outlet pathway |
| 160/560 | Mouth piece |
| 165/565 | Fritted glass |
| 170/570 | Liquid |
| 175/575 | Volatilizing chamber mount |
| 180/580 | Smoke Inlet Tube |
| 185/585 | Vapor aperture |

DETAILED DESCRIPTION

Reference is now made to the FIG. 1-5, wherein like parts are designated by like numerals throughout.

Figure 1:
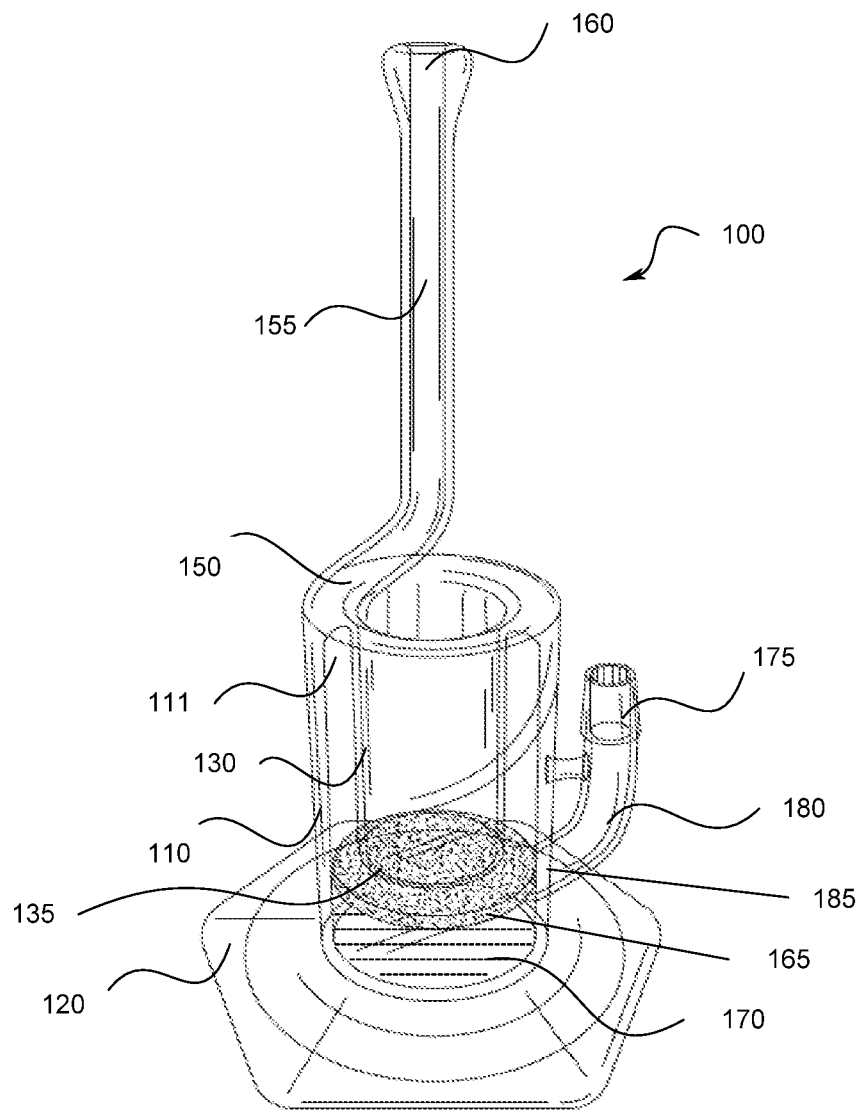
FIG. 1 is a perspective view of a water pipe apparatus.

With primary reference to FIG. 1, an embodiment of a water pipe 100 is a single piece construction, including a primary tubular wall 110 connected vertically to a base 120. The lowermost terminus of the primary tube 110 can be bonded or otherwise sealably secured to the base 120. The water pipe 100, further includes a secondary cylindrical tubular hollow glass wall structure 130 disposed inside the primary cylindrical tubular wall 110, vertically upon the base 120. The lower most terminus of the secondary tube can be sealed to a flat surface 135. An uppermost terminus of the tube 110 and an uppermost terminus of tube 130 are circumferentially sealed and make way for an aperture 150 which opens to a gas outlet pathway 155 leading to a mouthpiece 160 as indicated in FIG. 1.

A lower portion of the tube 110 is fitted with a fritted glass filter 165 above the base 120. In preparation for the use, the water pipe is filled with liquid 170, preferably water, in the space below the fritted glass filter 165. The water 170 occupying the lower portion of the tube 110 creates above its surface a compact smoke chamber 111 between the primary and secondary cylinder wall structures.

The tube 110 carries a smoke inlet tube 180 upon which is mounted with a bowl (not shown) on base joint 175 for vaporizing for volatilazable substance. The tube 180 provides an internal passage terminating in a smoke outlet aperture 185 into the water 170 at a point near to the bottom 120 of the tube 110. As described hereinafter, during operation of the water pipe, smoke is drawn through the passage of the tube 180 from the bowl (not shown) and emerges as bubbles from the lower end 185 of the tube 180.

A method of operation of the water pipe 100, referred in FIG. 1, is now described. The operator places volatile substance into the volatilizing vessel (not shown) and applies a lighted match, lighter or electric heater or the like thereto, until it is ignited and produces smoke or vapor. Medicinal herbs and or extracts may be employed in place of the tobacco in the bowl or volatizing vessel After the volatile material is ignited as described above, the user may exhale and then again place his mouth upon the end 160 of the tube 155, and then draw upon the tube 160 while excluding air from the water pipe 100. As the user draws upon the tube 160, volatiles or smoke from the bowl is drawn through the opening 185 into the tube 180 and emerges as bubbles from the tube 180. The bubbles of smoke are then buoyed upwardly through the water 170 in the lower portion of the tube 110, thereafter arriving into the chamber 111. Thus, a volume of smoke is formed in the compact chamber 111, cooled, scrubbed and freed of ash, tar and other contaminants by its passage through the water 170.

The volume of smoke in chamber 111, as the user continues to inhale, moves smoothly and uniformly without dilution by the incoming air into the mouth of the user, and thence through bronchial passages to the lungs of the user. The user therefore inhales an extended and substantially uniform puff of smoke pleasurably into his lungs.

With the waterpipe 100, after the user has inhaled the volume of smoke from chamber 111, he may continue to draw upon the waterpipe 100, thereby inhaling a following puff consisting of the cooled and moistened air which has displaced the smoke he has previously inhaled. This subsequent puff, free of smoke, cool and damp, provides soothing relief, if needed, from any caustic or stringent effects of the smoke upon his throat and bronchial membranes.

Figure 2:
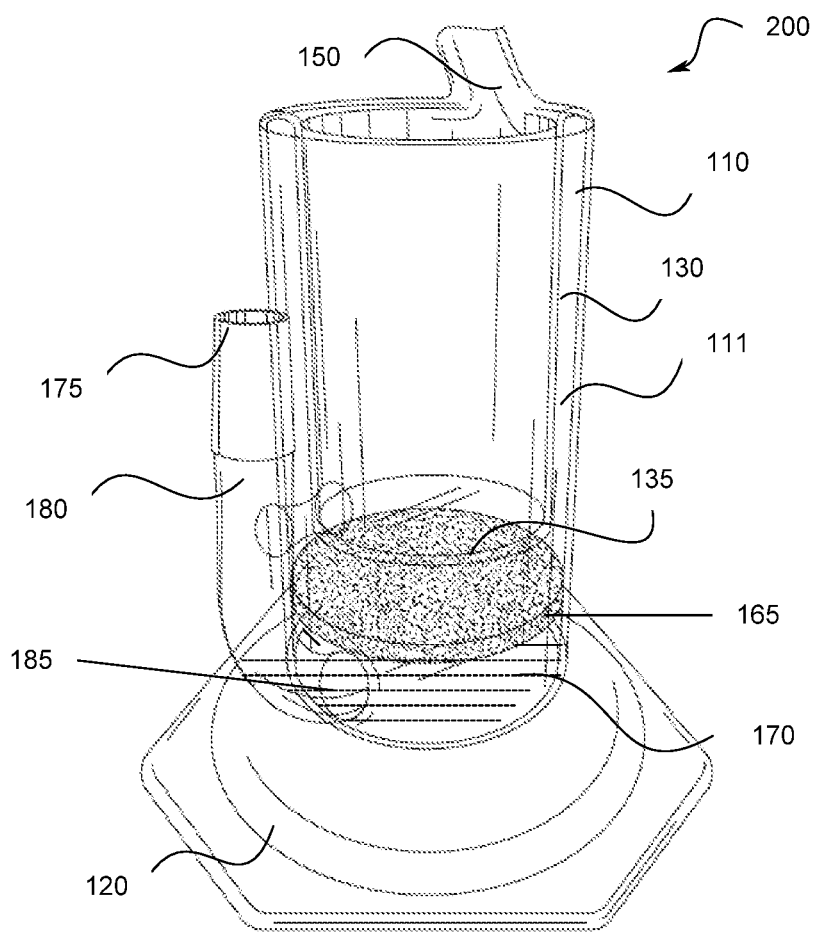
FIG. 2 is a closeup view of a water pipe apparatus.

Referring to FIG. 2, a close-up view 200 of the bottom portion is illustrated. It can be clearly seen that the water layer below the fritted glass makes way for an efficient scrubbing and cleaning of the gas bubbles emerging from the gas inlet tube and bouying into the gas outlet pathway.

Figure 3:
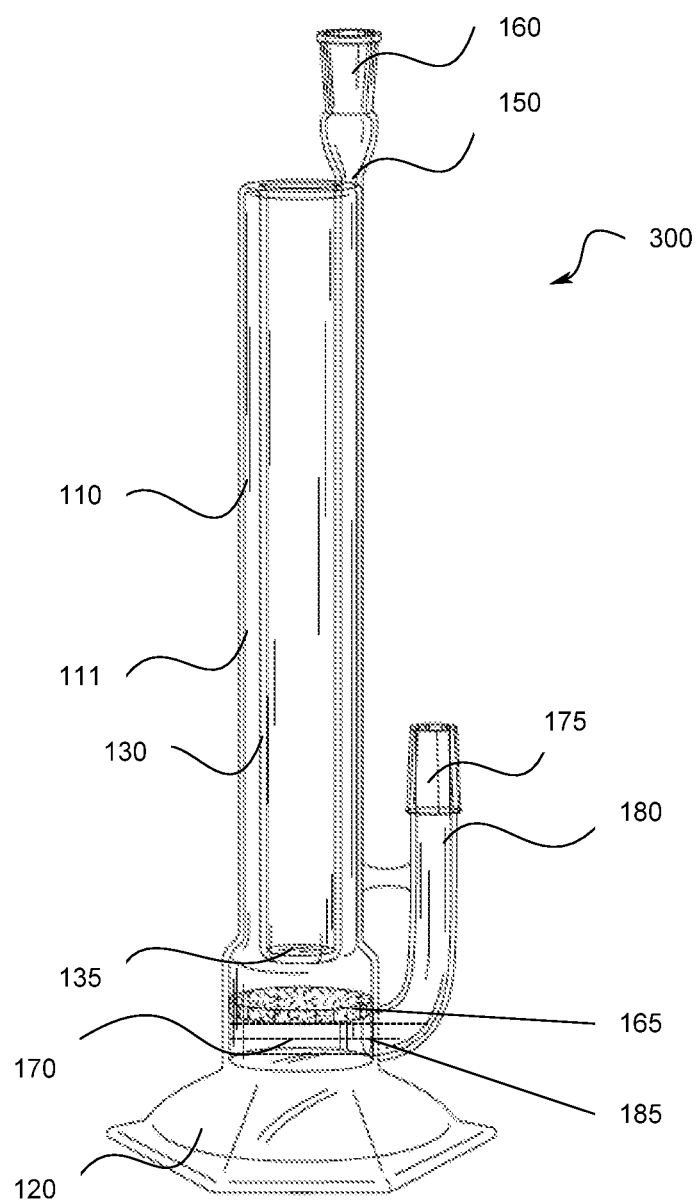
FIG. 3 is a perspective view of a water pipe apparatus.

With reference to FIG. 3, an embodiment of a water pipe designated by 300 is shown. In comparison to the water pipe 100 described above, the water pipe 300 has a lengthier cylindrical body and a very short inlet tube.

Figure 4:
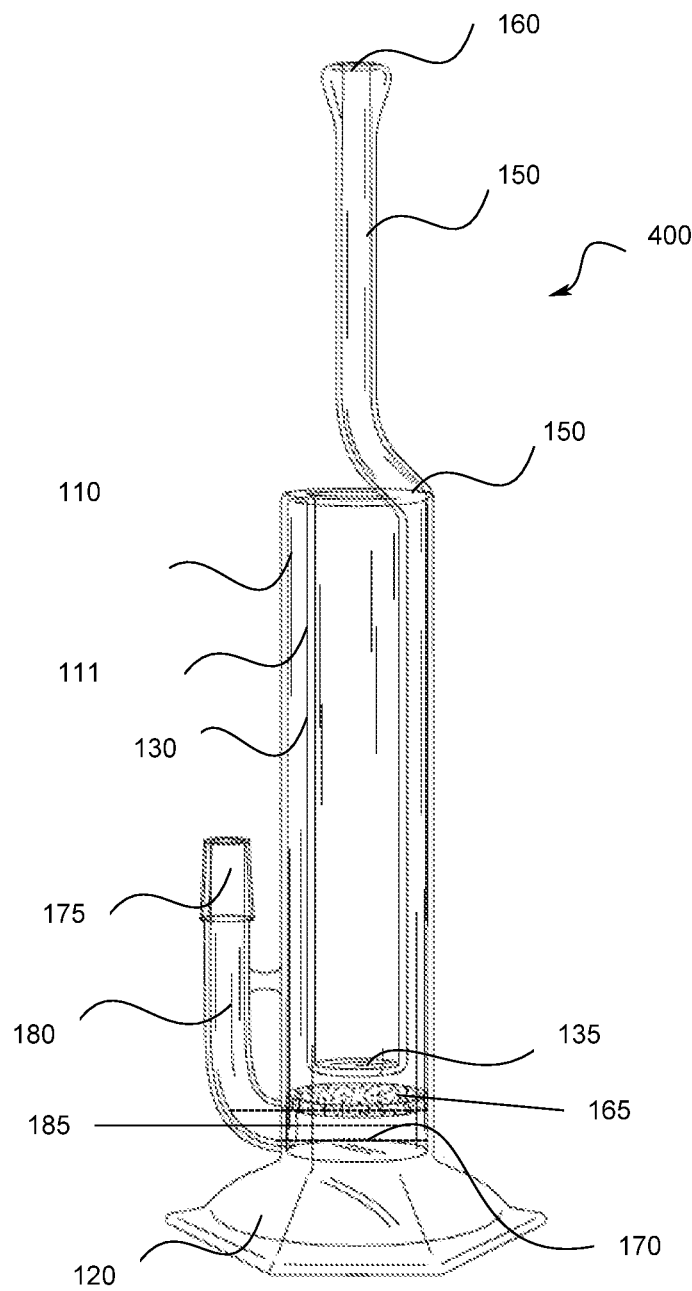
FIG. 4 is a perspective view of a water pipe apparatus.

With reference to FIG. 4, an embodiment of a water pipe designated by 400 is shown. In comparison to the water pipe 100 described above, the water pipe 400 has a lengthier cylindrical body and a lengthy inlet tube.

Figure 5:
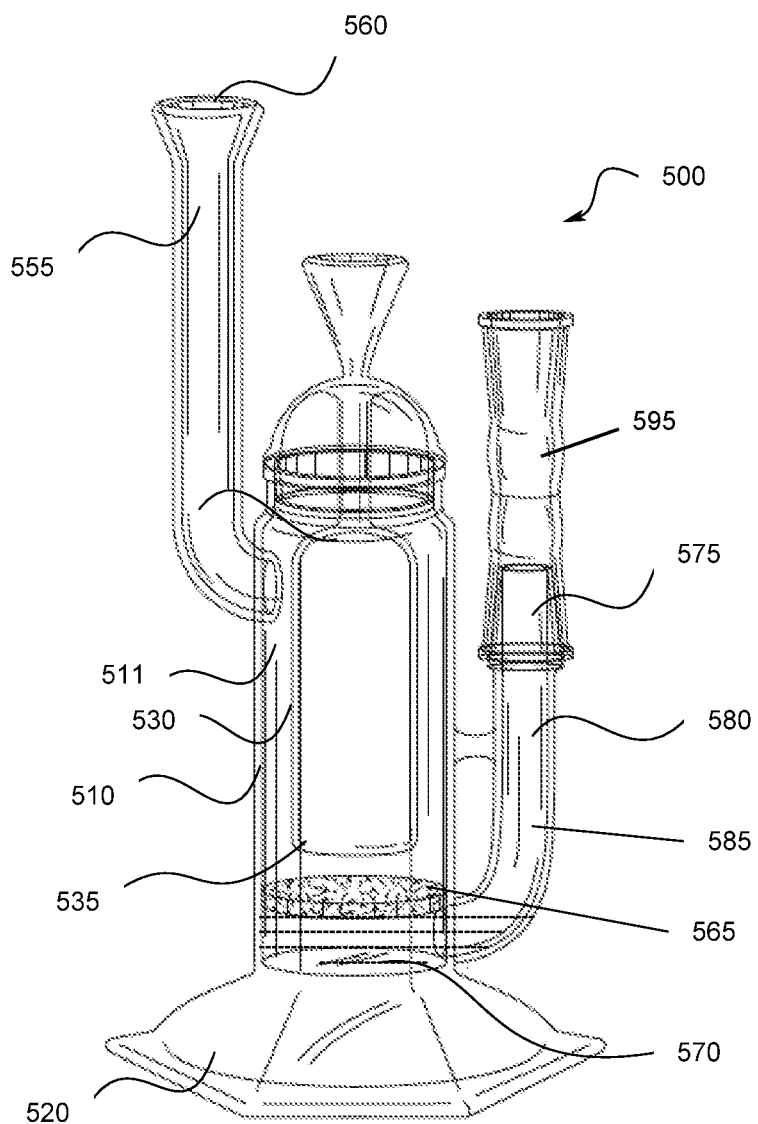
FIG. 5 is a perspective view of a water pipe apparatus.

With reference to FIG. 5, an embodiment of a water pipe 500, includes a primary cylindrical tubular wall 510 disposed vertically upon a base 520. The lowermost terminus of the primary cylindrical tubular wall 510 can be bonded or otherwise secured to the base 520.

The water pipe 500, has a secondary cylindrical tubular hollow glass structure 530 placed inside the primary cylindrical tubular wall 510, vertically upon the base 520, the lower most terminus of the secondary tube sealed to a flat surface 535. An uppermost terminus of the primary cylindrical tubular wall 510 has ground outer joint 540. The uppermost terminus of the secondary cylindrical tubular hollow glass structure 530 has ground inner joint 545 to mate with the ground outer joint of tube 510. The primary cylindrical tubular wall 510 has a side aperture 550 which opens to a gas outlet pathway 555 leading to a mouthpiece 560 as indicated in FIG. 5.

A lower portion of the primary cylindrical tubular wall 510 is fitted with a fritted glass filter 565 above the base 520.

In preparation for the use, the water pipe is filled with a liquid 570 preferably water. The water 570 occupying the lower portion of the tube 510 creates above its surface a compact smoke chamber 511 between the secondary cylindrical tubular hollow glass structure 530 and the primary cylindrical wall 510.

The primary cylindrical wall 510 carries a smoke inlet tube 580 upon which is mounted with a bowl or volatilizing chamber 595 for vaporizing a volatilizing substance. The tube 580 provides an internal passage terminating in a smoke outlet 585 beneath the surface of the water 570 at a point near the bottom 520 of the primary cylindrical wall 510. As described hereinafter, during operation of the water pipe, smoke or vapor is drawn through the passage of the tube 580 from the bowl or volatilizing chamber 595 and emerges as bubbles from the lower end 585 of the tube 580.

A method of operation of the water pipe 500, referred in FIG. 5, is now described. The operator places combustible substance into the volatilizing chamber 595 and applies a lighted match, lighter, electric heating or the like thereto, until it is ignited and produces smoke. Medicinal herbs may be employed in place of the tobacco in the volatilizing chamber 595.

After the combustible material is ignited as described above, the user may exhale and then again place his mouth upon the end 560 of the tube 555, and then draw upon the tube 560 while excluding air from the water pipe 500. As the user thus draws upon the tube 560, smoke or vapor or gaseous effluent from the bowl or volatilizing chamber 595 is drawn through the opening 585 in the tube 580 and gaseous effluent emerges as bubbles from the tube 580. The bubbles of smoke are then buoyed upwardly through the water 570 in the lower portion of the tube 510, thereafter arriving into to the chamber 511. Thus, a volume of smoke is formed in the compact chamber 511, cooled, scrubbed and freed of ash, tar and other contaminants by its passage through the water 570.

The volume of smoke in chamber 511, as the user continues to inhale, moves smoothly and uniformly without dilution by the incoming air into the mouth of the user, and thence through bronchial passages to the lungs of the user. The user therefore inhales an extended and substantially uniform puff of smoke or vapor pleasurably into his lungs. In contrast to the water pipe 500, other water pipes and bongs hereinbefore described with air admitting orifices directly into the smoke containing chamber 511 above the surface of the water provide the user with a puff of smoke successively diluted and weakened as the user continues to inhale. This is because air admitted into the chamber 511 through a side wall thereof strongly tends to mix with and dilute the smoke therein. The user using such a water pipe accordingly never completely exhausts the chamber 511 of all smoke.

The design features for water pipe 100/300/400500 may be selected in size and proportions in accordance with the individual user's desires. It is desirable and efficient to use cylindrical tubular members to form the water and smoke containing chamber. However, chambers otherwise shaped may be used without departing from the spirit of the invention, so long as such shapes are chosen to be consistent with the operation of the water pipe as herein described. Thus, the uniform displacement and inhalation of smoke could be preserved by the use of a chamber 511 which tapered from larger to smaller in the vertical direction. However, the use of an extremely bulbous of pot shaped smoke chamber would tend to defeat this feature of the operation. As a further example, a pot or bulb shaped water chamber could probably be employed, but such a chamber would more desirably be shaped to blend smoothly at the surface of the water with the lowermost extension of the smoke inhalation chamber.

It is clear that a variety of designs could be employed for the mouthpiece 160/560 without departing from the spirit of the invention. For example, the tube 155/555 could be narrowed at the end 160/560, so that the lips of the user could embrace, rather than be embraced, by the mouthpiece as in the illustrated embodiments. Likewise, standard taper ground fittings may allow for accessorizing as desired.

As indicated in both FIGS. 1-4 and 5, the chamber forming tubes 110/510 and 130/530 may be transparent, so that the user may observe the passage, bubbling and accumulation of the smoke during the above described sequences. It is clear however that the use of opaque members would not in any way depart from the spirit of the invention.

The porosity of a frit is related to the mesh range of the glass beads (particles) or fibers. The mesh range of glass beads or packing determines a nominal particle size: For example, a 200-400 mesh corresponds to 37-74 .mu.m, and are sometimes called out as 40 .mu.m. This means that a frit with a pore size of 16-40 .mu.m will not clog when used to support a nominal 40 .mu.m packing. Commonly, a frit may be classified as a medium porosity frit having 10-15-.mu.m porosity, a coarse porosity frit having a 40-60 .mu.m porosity, or an extra-coarse porosity frit having a 170-220 .mu.m porosity.

In a preferred embodiment, the present invention contemplates a glass laboratory apparatus filtration device having a filter. The filter could be a fritted disk, a stainless-steel mesh screen or a carbon fiber filter or an activated charcoal filter or another similar filtering device.

One use of the present invention includes filtering gas or vapor, such as tobacco. A vaporizing or volatilizing sample of burning tobacco is placed in the volatilizing structure and ordinary water is placed in the vessel as the liquid 170 or 570. This is known as water filtration and there is substantial epidemiological evidence of lower incidences of carcinoma among tobacco users using water filtration compared to other methods of inhaling tobacco products—i.e. from a cigarette, pipe, or cigar. The gas-dispersion frit 165 or 565 serves to break up the smoke, gas, and/or vapor into very fine bubbles, thereby increasing its water-contact area. Frits are commonly referred to as "diffusers" for the way that they diffuse (or disperse) the particulates suspended in the gas as it exits the vessel.

In other contemplated embodiments, the shape of the vessel can be modified to a bulged bottom dual walled coaxial cylinders or a bulged top dual walled coaxial cylinder or a dual walled coaxial sphere or the like.

In other contemplated embodiments, the fritted disc may be substituted with any-filter device including a porous, incombustible pre-filter and can be configured in the vessel, for example by inverting a cone of an upturned standard-taper inner joint to form a support shelf for aforementioned pre-filter.

A fluid, or more precisely, a gas conduit is formed by the linking or coupling from the gas inlet pathway 180/580 to the gas outlet pathway 155 or 555. Thus, when a pressure differentiation is affected (lower pressure at the exhaust) a gas is forced through the fritted disc 165 or 565 through the liquid solution 170 or 570 and up through the gas outlet structure 160 or 560.

As such, the apparatus of the present invention is well suited for scrubbing a gas of undesired particles, solids, and other impurities. Another benefit, if used with water in the main chamber, is the cooling effect of the water and that the water can trap some heavier particles and water-soluble molecules, preventing them from entering the effluent stream.

The apparatus of the present invention is well suited for scrubbing a gas of undesired soluble, particles, solids, and other impurities. Another benefit, if used with water in the main chamber, is the cooling effect of the water and that the water can trap some heavier particles and water-soluble molecules, preventing them from entering the effluent stream.

The present invention can be altered physically to affect the needed pressure differential to cause bubble filtration through the filter. The greater the volume of water, the greater the pressure differentiation required scrubbing the gas. The defined range of pressure differential is limited by water column height, which should not exceed the height of the pre-filter, as it works poorly when wet. Additionally, allowing the combusted remains to get wet would create recovery, purity and cleaning related issues for the user.

In an preferred embodiment, a laboratory apparatus 100/300/400/500 consists of blown glass, specifically the apparatus is fabricated from borosilicate glass tubing, 33-expansion type and may include two filters, preferably a first (pre-filter) fritted disc and second fritted disc, however the pre-filter could also be a stainless-steel mesh screen or any incombustible yet porous substance, as would be appreciated by those skilled in this art. Each disc is fabricated by filling vermiculite molds commercially available clear borosilicate frit, large size (#25 mesh) as supplied, for example by North Star Glass and/or Glass Alchemy (both located in Portland, Oreg., USA). While disks can be made from a variety of mold materials, plaster and vermiculite board are the most practical materials.

To avoid significant breakage of the fritted discs, a kiln wash/glass release using kaolin clay and alumina hydrate is painted the slurry on the quartz rings, dried it out, and then filled the rings with frit. Moreover, a glass release compound of kaolin clay and alumina hydrate slurry is applied to all mold surfaces to prevent damage to both molds and fritted ware upon release, as would be well understood by those skilled in this art.

The fritted discs can be made in small batches or, alternatively, for larger production quantities, from flat plate stock that has been core-drilled to the proper diameter so that many mold orifices can be filled quickly from bulk. Further economies can be gained from using a kiln wash as an effective substitute for more expensive and time-consuming kiln paper covering the vermiculite mold.

FIG. 1-5 shows a base 120/520 connected or fused to the vessel at a lower portion. The base aids in supporting the vessel on a level surface and, accordingly can be any shape. One contemplated shape is a hexagonal base, another contemplated shape is a six-pointed concave hexagon with curved line segments joining each adjacent point of the six points, each point equally distant from the bases geometric center; although those skilled in the art would appreciate that additional configurations for the base would work equally well. Not shown in the drawings, but contemplated nevertheless: A supporting member adapts to connect the inlet portion to the main body of the vessel, this supporting member is not in fluid connection with the inlet and outlet, but serves merely to mechanically strengthen and reduce the propensity for damage and breakage of the inlet tube portion relative to the main vessel body.

The embodiments of the present invention presented herein are for illustrative purposes only and are not intended to restrict the scope of the invention in any way, any embodiment of the invention within the scope and breadth of the appended claims being intended to be embraced thereby. All embodiments within the meaning and range of equivalency of the appended claims are intended to be embraced therein. The invention may be embodied in other specific forms than those illustrated or mentioned herein without departing from the spirit or essential characteristics thereof.

The invention claimed is:

1. A glassware apparatus comprising:
   a water pipe of single-piece construction having a mouth piece in fluid communication with a compact chamber of the water pipe,
   the water pipe comprising:
      a cylinder inbuilt within the water pipe, wherein the cylinder comprises a flat surface on
      a first end and an open duct on a second end, the cylinder formed concentrically within
      a circumference of the water pipe, each the water pipe and the cylinder having a center in planar alignment;
      an aperture in fluid communication with a smoke inlet tube, the smoke inlet tube having a volatizing chamber mount, the volatizing chamber mount disposed in a plane lower than a plane of the mouth piece;
      a secondary wall of the cylinder disposed in parallel with a primary wall of the water pipe defining the compact chamber between the primary wall and the secondary wall;
      a fritted porous glass filter disposed within a void between an underside of the flat surface of the first end of the cylinder and a base of the water pipe, the base disposed at a bottom end of the water pipe opposite the mouth piece; and
      a liquid disposed between the fritted porous glass filter and the base of the water pipe;
   wherein the glassware apparatus further comprises a volatizing chamber removably coupled to the water pipe via the volatizing chamber mount such that the volatizing chamber is in fluid communication with the volatizing chamber mount.

2. The glassware apparatus of claim 1, wherein the compact chamber is inbuilt into the water pipe.

3. The glassware apparatus of claim 2, wherein the water pipe is made of borosilicate glass.

4. The glassware apparatus of claim 3, wherein the liquid is water.

5. The glassware apparatus of claim 4, wherein the base comprises a six-pointed generally hexagonal shaped support of the water pipe having rounded vertices, a top side, and a bottom side.

6. The glassware apparatus of claim 5, wherein the fritted porous glass filter has an average porosity range between 85 to 95 micrometers.

7. A glassware apparatus comprising:
   a water pipe of single-piece construction having a compact chamber disposed between a mouth piece and a volatizing chamber mount, the compact chamber in fluid communication with the mouth piece and the volatizing chamber mount; the volatizing chamber mount disposed in a plane lower than a plane of the mouth piece;
   the compact chamber comprising:
      a secondary cylindrical wall;
      a primary cylindrical wall disposed in a substantially coaxial configuration around the secondary cylindrical wall to define the compact chamber in an annulus region formed between the primary cylindrical wall and the secondary cylindrical wall, the primary cylindrical wall and the secondary cylindrical wall each having an upper portion and a bottom portion,
      the upper portion of the primary cylindrical wall and the upper portion of the secondary cylindrical wall comprising: a first aperture in fluid communication with a gas outlet pathway and the mouth piece;
      the bottom portion of the primary cylindrical wall comprising;
         a second aperture in fluid communication with a smoke inlet tube connected to the volatizing chamber mount;
      a flat surface formed within the first bottom portion of the secondary cylindrical wall;
      a fritted porous glass filter disposed between the bottom portion of the primary cylindrical wall and the bottom portion of the secondary cylindrical wall;
      a liquid disposed between the fritted porous glass filter and a base;
   wherein the glassware apparatus further comprises a volatizing chamber removably coupled to the water pipe via the volatizing chamber mount such that the volatizing chamber is in fluid communication with the volatizing chamber mount.

8. The glassware apparatus of claim 7, wherein the compact chamber is inbuilt into the glassware apparatus.

9. The glassware apparatus of claim 8, wherein the glassware apparatus is made of borosilicate glass.

10. The glassware apparatus of claim 9, wherein the base comprises a six-pointed generally hexagonal shaped support of the glassware apparatus having rounded vertices, a top side, and a flat bottom side.

11. The glassware apparatus of claim 10, wherein the fritted porous glass filter has an average porosity range between 85 to 95 micrometers.

* * * * *